United States Patent
Yanai et al.

(10) Patent No.: US 6,773,701 B2
(45) Date of Patent: Aug. 10, 2004

(54) EXPRESSION ENHANCER FOR PROTEIN SYNTHESIS INHIBITORY GENES

(75) Inventors: Yoshiaki Yanai, Okayama (JP); Osamu Sano, Okayama (JP); Masashi Kurimoto, Okayama (JP)

(73) Assignee: Kabushiki Kaisha Hayashibara Seibutsu Kagaku Kenkyujo, Okayama (JP)

(*) Notice: Subject to any disclaimer, the term of this patent is extended or adjusted under 35 U.S.C. 154(b) by 0 days.

(21) Appl. No.: 09/962,625

(22) Filed: Sep. 26, 2001

(65) Prior Publication Data

US 2003/0039629 A1 Feb. 27, 2003

(30) Foreign Application Priority Data

Oct. 27, 2000 (JP) ........................................ 2000-328539
Apr. 16, 2001 (JP) ........................................ 2001-116710

(51) Int. Cl.$^7$ ........................ A61K 38/21; A61K 45/00; A61K 38/00; C07K 17/00; C07K 14/00
(52) U.S. Cl. ................... 424/89.7; 424/85.1; 424/85.4; 514/2; 530/351; 530/350
(58) Field of Search .............................. 424/85.7, 85.1, 424/85.4; 514/2; 530/351, 350

(56) References Cited

U.S. PATENT DOCUMENTS

| | | | |
|---|---|---|---|
| 3,912,591 A | | 10/1975 | Kato et al. |
| 4,276,282 A | | 6/1981 | Sugimoto et al. |
| 4,372,883 A | | 2/1983 | Matuhashi et al. |
| 5,780,021 A | * | 7/1998 | Sobel .......................... 424/85.4 |
| 6,010,871 A | | 1/2000 | Takahara et al. |

FOREIGN PATENT DOCUMENTS

| | | |
|---|---|---|
| EP | 0 416 816 A1 | 3/1991 |
| EP | 0 658 627 A2 | 6/1995 |
| EP | 0 586 034 B1 | 8/2000 |
| JP | 49-42894 | 4/1974 |
| JP | 56-39022 | 4/1981 |
| JP | 56-54158 | 12/1981 |
| JP | 3-93730 | 4/1991 |
| JP | 6-65302 | 3/1994 |
| JP | 7-163368 | 6/1995 |
| WO | WO 96/10089 A1 | 4/1996 |

OTHER PUBLICATIONS

Johnson et al., May 1994, Scientific American, pp. 68–75.*
Robin E. Callard et al., *The Cytokine FactsBook*, San Diego: Academic Press Inc., 1994, pp. 146–162.

De Maeyer et al., "Chapter 18: Interferons", *The Cytokine Handbook*, Third Edition, Edited by Angus W. Thomson, San Diego: Academic Press Inc., 1998, pp. 492–516.

Triozzi et al., "Induction of 2',5'–Oligoadenylate Synthetasae Activity in Peripheral Blood Mononuclear Cells by Gamma Interferon", *Journal of Biological Response Modifiers*, 1986, pp. 562–570, vol. 5.

Coccia et al., "Interferons–α/β–and –ν–Resistant Friend Cell Variants Exhibiting Receptor Sites for Interferons but No Induction of 2–5A Synthetase and 67 K protein Kinase", *Journal of Interferon Research*, 1988, pp. 113–127, vol. 8.

Allen et al., "Nomenclature of the Human Interferon Proteins", *Journal of Interferon and Cytokine Research*, 1996, pp. 181–184, vol. 16.

Imanishi et al., "New Simple Dye–Uptake Assay for Interferon", *Biken Journal*, 1981, pp. 103–108, vol. 24.

Chou, "Chapter 2: The Median–Effect Principle and the Combination Index for Quantitation of Synergism and Antagorism", from *Synergism an Antagonism in Chemotherapy*, pp. 61–102, Academic Press, Inc., 1991.

Hiraki et al., "Establishment of an Epstein–Barr Virus–Determined Nuclear Antigen–Negative Human B–Cell Line from Acute Lyphoblastic Leukemia: *Brief Communication*", *J. Natl. Cancer Inst.*, Jul. 1977, pp. 93–94, vol. 59, No. 1.

Diaz et al., "Nomenclature of the Human Interferon Genes", *Journal of Interferon and Cytokine Research*, 1996, pp. 179–180, vol. 16.

Jikken–Igaku–Bessatsu–Biomanual–Up–Series, basic Technique for Gene Therapy, edited by Shimada et al., Tokyo, Japan, 1996.

"Proceedings of the Japanese Society for Immunology", vol. 30, Sep. 26, 2000.

* cited by examiner

*Primary Examiner*—Janet Andres
(74) *Attorney, Agent, or Firm*—Browdy and Neimark, P.L.L.C.

(57) ABSTRACT

The objects of the present invention are to reveal a specific combination of human interferon-α subtypes that remarkably enhances the expression of protein synthesis inhibitory genes, and to provide an expression enhancer comprising as effective ingredients interferon-α subtypes in such a combination and uses thereof. The above objects are solved by providing an expression enhancer for protein synthesis inhibitory genes which comprises as effective ingredients interferon-α2 and interferon-α8 subtypes of human interferon-α, and uses thereof including pharmaceuticals.

1 Claim, No Drawings

EXPRESSION ENHANCER FOR PROTEIN SYNTHESIS INHIBITORY GENES

TECHNICAL FIELD

The present invention relates to a novel expression enhancer for protein synthesis inhibitory genes, more particularly, to an expression enhancer for protein synthesis inhibitory genes, which comprises as effective ingredients interferon-α2 and interferon-α8 subtypes of human interferon-α (hereinafter the terms "interferon", "interferon-α", "interferon-α2 subtype of human interferon-α", and "interferon-α8 subtype of human interferon-α" may be abbreviated as "IFN", "IFN-α", "IFN-α2" and "IFN-α8", respectively).

BACKGROUND ART

The term IFN(s) is the generic name for a group of proteins having anti-virus activity secreted extracellularly from vertebrate animal cells when externally stimulated by virus infections or antigenic stimulants. Based on the antigenicity of IFNs, they are roughly classified into three types of IFN-α, IFN-β and IFN-γ. IFNs have been known to have anti-virus activity and other diversified physiological activities such as cell growth-inhibitory activity and anti-tumor activity. The isolation and identification of receptors against IFNs have been progressed and, for example, as disclosed in "*The Cytokine FactsBook*", edited by Robin E. Callard and Andy J. H. Gearing, published by Academic Press, pp. 148–162 (1994), it is known that IFN-α and IFN-β have a common receptor and that IFN-γ has another different acceptor. Similarly as in the case of other cytokines, the expression of physiological activities of IFNs is caused by different changes in IFN-susceptive cells induced by IFN stimulations in such a sequential manner of the binding of IFNs to their receptors expressed on the cell surfaces, the actuation of intracellular information transmission system, and the intracellular expression of specific genes. The isolation and identification of molecules relating to the above intracellular information transmission system has been in a rapid progress in these days.

There are different types of genes whose gene expressions are induced as a result of cell stimulation by IFNs. For example, Table 2 in chapter 18 of "*The Cytokine Handbook*", 3rd edition, edited by Angus Thomson, published by Academic Press (1998) shows products or proteins as gene expression products, induced by the stimulation of IFN-α and IFN-β, such as 2', 5'-oligoadenylate synthetase (abbreviated as "2–5A" hereinafter), double-stranded RNA dependent protein kinase (hereinafter abbreviated as "PKR"), Mx protein, class I and class II MHC molecules, β-2 macroglobulin, guanylate bound proteins, and metallothionein. Most of the above products or proteins can be also induced by IFN-γ. Among these gene expression products induced by IFNs, 2–5A synthetase and PKR as protein synthesis inhibitory enzymes, and Mx protein play a direct role in inhibiting abnormality of cells received with abnormal conditions such as tumorigenic transformation and virus infection. While MHC molecules and β-2 macroglobulin are proteins responsible for the function of immune system of living bodies, and indirectly relate to the elimination of tumors and viruses from the bodies through the action of immune system in vivo. As regards guanylate bound proteins and metallothionein, their correlations with the expression of physiological activities by IFN(s) have not been revealed yet.

At the beginning of the discovery, IFN was once called "a novel dream medicine" and had been greatly expected for use as a pharmaceutical, however, there found no sufficient therapeutic effect on some types of diseases as it had been expected. As one of the causes thereof, it may be speculated that although there exist specificities on the actions and levels to be exerted depending on the conditions of the types and subtypes of IFNs used, for example, the types of cells to be treated and of viruses being infected to the cells and the combination of IFNs used, it has not yet been completely revealed the optimum conditions for sufficiently exerting the desired actions in respective conditions.

As regards the comparison among the gene expression enhancing actions by IFN-α, IFN-β and IFN-γ, for example, as found in "*Journal of Biological Response Modifiers*", Vol. 5, No. 6, pp. 562–570 (1986) by PL. Triozzi, and "*Journal of Interferon Research*", Vol. 8, No. 1, pp. 113–127 (1988) by EM. Coccia et al., it was reported that IFN-γ was inferior to IFN-α and IFN-β in expression inductivity of 2–5A synthetase gene and PKR gene. On the contrary, unlike IFN-β and IFN-γ, IFN-α has at least ten or more subtypes, however, there has been no report on research aiming at revealing the action conditions of IFN-α to effectively exert its gene expression enhancing action, particularly, the optimization of combination use of IFN-α subtypes.

DISCLOSURE OF INVENTION

Under the above background, the present inventors focused their attention on the fact that there has not yet been studied a research on products, which are expressed by protein synthesis inhibitory genes through the induction by IFNs and which directly relate to exert some actions by IFNs, nor a research on the optimization of the combination use of IFN-α subtypes in inducing the expression of the genes. Based on this, they speculated that, if an appropriate combination of IFN-α subtypes that greatly enhances the expression of the genes were found, more effective medical uses of such IFNs would be attained.

Thus the object of the present invention is to specify the combination use of IFN-α subtypes that outstandingly enhances the expression of protein synthesis inhibitory genes, and to provide a gene expression enhancer comprising, as effective ingredients, the above IFN-α subtypes used in combination and uses thereof.

To attain the above object, using isolated human IFN-α subtypes, the present inventors widely studied the action of the subtypes on cells when used alone or in combination, and then compared the results each other. As a result, the present inventors found the following completely novel phenomenon: When IFN-α2 and IFN-α8 subtypes of human IFN-α are allowed to act on cells in combination, they synergistically enhance the expression level of protein synthesis inhibitory genes such as 2–5A synthetase intracellularly. This phenomenon was evidenced by the fact that the phenomenon was also observed as a synergism when examined with an index of anti-virus activity to which 2–5A synthetase would directly correlate. The present invention was made based on the above completely novel finding by the present inventors.

The present invention solves the above objects by providing an expression enhancer for protein synthesis inhibitory genes which comprises as effective ingredients IFN-α2 and IFN-α8 subtypes of human IFN-α, and uses thereof including pharmaceuticals.

BEST MODE OF THE INVENTION

The present invention relates to an expression enhancer for protein synthesis inhibitory genes (may be referred to as "the expression enhancer of the present invention" or "the expression enhancer", hereinafter) which comprises as effective ingredients IFN-α2 and IFN-α8 subtypes of human IFN-α (the term "IFN-α2 and IFN-α8 subtypes of human IFN-α" may be briefly called "subtypes"). The terms "IFN-α2" and "IFN-α8" as referred to as in the present invention mean proteins which contain substantially the same amino acid sequences of the subtypes containing the N-terminal signal sequences as shown in SEQ ID NOs: 1 and 2 in the present specification, registered for SWISSPROT, a protein database produced by Amos Bairoch, Switzerland, under the primary accession numbers of P01563 and P32881, respectively, and which are confirmed to have anti-virus activity when determined in the later described appropriate assay systems, independently of their higher-order structures and carbohydrate chains other than their amino acid sequences. The term "substantially the same amino acid sequences" as referred to as in the above means that the amino acid sequences of subtypes used can be classified into those of human IFN-α and have the highest possible homology to the amino acid sequence of SEQ ID NO:1 or 2 when compared with the conventional amino acid sequences of IFN-α subtypes. The conventional amino acid sequences of human IFN-α subtypes are, for example, summarized by G. Allen et al., in "Journal of Interferon and Cytokine Research", Vol. 16, pp. 181–184 (1996) with citations of original reports on respective amino acid sequences. The literature shows that IFN-α2 subtype includes a protein with the amino acid sequence of SEQ ID NO:1 and another two types of proteins with SEQ ID NO: 1 but different in one amino acid residue, and that IFN-α8 subtype includes a protein with the amino acid sequence of SEQ ID NO:2 and another two types of proteins with SEQ ID NO:2 but different in four or six amino acid residues. The IFN-α2 and IFN-α8 subtypes as referred to as in the present invention should not be restricted to the amino acid sequences of SEQ ID NOs:1 and 2 and may include those which have different amino acid residues from the amino acid sequence of SEQ ID NO:1 or 2, usually, at positions not more than 10, preferably, not more than eight, and more preferably, not more than six in SEQ ID NO:1 or 2.

Any subtypes can be used in the present invention independently of their origins and preparation methods as long as they are the IFN-α2 and IFN-α8 subtypes as defined above. For example, advantageously used are naturally-occurring subtypes from human cells, recombinant subtypes prepared by conventional genetic engineering techniques using vertebrate cells including human cells, invertebrate cells, plant cells, and microorganisms including procaryotic cells such as *Escherichia coli* and Bacilli and eucaryotic cells such as yeasts and fungi. In addition, naturally or artificially produced subtypes having the later described water-soluble macromolecules covalently coupled to the polypeptide chains of IFN-α2 and/or IFN-α8 subtypes (may be called "modified products with water-soluble macromolecules", hereinafter), can be also used advantageously as long as they retain the inherent activity of the subtypes. The subtypes in the form of modified products with water-soluble macromolecules include, for examples, naturally-occurring subtypes with water-soluble macromolecules and others, prepared by artificially binding water-soluble macromolecules covalently to previously prepared natural or recombinant subtypes, can be advantageously used, as long as they retain the inherent activities of IFN-α2 and IFN-α8 subtypes. However, the later described subtypes in the form of modified products with water-soluble macromolecules obtainable by artificial techniques have an advantageous features that they are relatively superior in stability level in living bodies to be administered when used in medical uses for administering to patients to be treated. The use of naturally-occurring subtypes would be advantageous, for example, because of their relatively low antigenicity to patients, while recombinant subtypes have the advantage of being produced or available in a relatively lesser cost. Therefore, in practicing the present invention, suitable subtypes can be selected among these subtypes while considering their features to meet purposes in use.

The confirmation whether the subtypes used in the present invention are IFN-α2 and IFN-α8 subtypes is made by assigning with the amino acid sequences of SEQ ID NOs:1 and 2 either partial amino acid sequences obtained by conventionally decoding subtypes to be assigned, or amino acid sequences estimable from nucleotide sequences obtained by isolating and decoding cDNAs corresponding to the amino acid sequences of subtypes from their sources.

The activity (titer) of IFN-α is usually expressed in terms of international unit (may be abbreviated as "IU", hereinafter) based on anti-virus activity in comparison with an IFN-α standard specimen. An international human IFN-α standard specimen is provided as "Ga23-901-532" in the form of a sealed ample containing 25,000 IU of IFN-α from the National Institutes of Health (NIH). Anti-virus activity can be determined by different methods. For example, the anti-virus activity can be quantitatively confirmed as inhibitory activity of IFN-α against the cytopathic effect (may be abbreviated as "CPE", hereinafter) by viruses on cells using the dye uptake method described by J. Imanishi et al. in "*Biken Journal*", Vol. 24, pp. 103–108 (1981). Throughout the present specification, the IFN-α activity is expressed as IU, assayed according to the above method using Sindbis virus as a virus and FL cells (ATCC CCL-62), an established cell line derived from human amnion cell, as a cell. The theory of the assay is as follows: Firstly, the concentration X (IU/ml) of the above international standard specimen that inhibits 50% of CPE induced by Sindbis virus on FL cells is determined, then under the same conditions the concentration Y (mg/ml) that inhibits 50% of CPE with a testing specimen containing IFN-α to be assayed. Based on the data, the activity Z (Iu/mg) per milliliter of the testing specimen is calculated by the equation of Z=X/Y. The specific activity (Iu/mg protein) of IFN-α can be determined by combining the activity determined by the equation and the result of quantified protein amount.

The protein synthesis inhibitory gene as referred to as in the present invention means a gene encoding a protein having a function that inhibits or suppresses intracellular reactions relating to intracellular protein synthesis of either transcription from DNAs to mRNAs or translation of proteins from mRNAs, and usually means one whose expression is induced by the stimulation of IFN-α. The above transcription step includes all intracellular reactions, that form functional mRNAs having sequences corresponding to template DNAs, such as the formation of primary transcription products from DNAs, splicing of RNAs, and the addition of cap structure to RNAs and of polyadenylate. The above translation step includes all intracellular reactions, that form polypeptides having sequences corresponding to mRNAs, such as the initiation of protein biosynthesis initiated by the binding of liposome onto mRNAs, the elongation of polypeptide chains that link amino acids according to the genetic codes encoded by mRNAs, and the termination of protein biosynthesis by the termination codons on mRNAs. Concrete examples of the protein synthesis inhibitory genes applicable to the present invention are, for example, 2–5A synthetase gene and PKR gene. 2–5A Synthetase, as a product of the above gene, forms intracellularly 2–5A using ATP as a substrate, then 2–5A converts ribonuclease L in an inactive form present in cells into an active form, and the activated ribonuclease decomposes RNAs to inhibit the synthesis of proteins. While PKR inhibits the synthesis of proteins by phosphorizing to inactivate the $\alpha$ subunit of eIF-2 as a factor, which relates to the initiation of protein biosynthesis as mentioned above, depending on double-stranded RNAs.

The term "the induction of gene expression by the stimulation of IFN" means that the expression level of intracellular genes is observed as an increase of the transcription level of genes and/or the translation level of mRNAs in correspondence with the stimulation of cells by IFN. Varied depending on the types of genes and cells with such genes, the protein synthesis inhibitory genes as referred to as in the present invention are increased their expression levels usually by at least 1.5-times, preferably, at least 2-times, and more preferably, at least 2.5-times by the stimulation of IFN. To compare the gene expression level with the transcription level, for example, conventional quantitative RT-PCR and northern blot technique can be used; Since the nucleotide sequences of the above exemplified genes have been registered for GenBank under the accession codes in Table 1, the transcription level of the desired genes can be detected sensitively and quantitatively by practicing the above methods using primers and probes prepared based on the above registered nucleotide sequences. To compare the gene expression level with the translation level, it can be practiced by the methods for specifically quantitating proteins as gene expression products, for example, immunoassays when specific antibodies against the testing gene expression products are available, appropriate assays for enzymatic activity when the testing gene expression products have an enzymatic activity, and appropriate bioassays when the testing gene expression products have a physiological activity.

TABLE 1

| Gene expression product | Accession codes for nucleotide sequence |
| --- | --- |
| 2-5A Synthetase | NM_016817, NM_002534, NM_016816 NM_006187, NM_002535 |
| PKR | AH008429 |

The expression enhancer of the present invention comprises IFN-$\alpha$2 and IFN-$\alpha$8 subtypes as effective ingredients and has characters that it exerts either the sum action of the expression induction action exerted by subtypes, respectively; or the action that clearly exceeds the estimated sum action, i.e., a synergism in inducing the expression of protein synthesis inhibitory genes. Such a synergism can be confirmed by the transcription and translation levels calculated as above. The expression products of protein synthesis inhibitory genes as referred to as in the present invention are usually major functional molecules which exhibit physiological activity of IFN-$\alpha$ exerted on IFN-$\alpha$ sensitive cells, and therefore such a synergism can be confirmed by a synergism of the expression of physiological activities of IFN-$\alpha$, for example, the expression of anti-virus activity, cell growth inhibitory activity, and apoptosis induction activity, observed in the IFN-$\alpha$ sensitive cells when the expression enhancer of the present invention is allowed to act on the cells. For example, the apoptosis activity can be confirmed by conventional methods in such a manner of allowing the expression enhancer of the present invention to act on cancer cells such as of hepatic carcinoma, and quantitatively observing the fragmentation of intracellular DNAs as a characteristic phenomenon of apoptosis, and the expression of apoptosis-related-molecules such as Fas. Since the expression enhancer of the present invention synergistically, greatly enhances even the expression induction action of protein synthesis inhibitory genes by IFN-$\gamma$, it can be also used as an enhancer for the expression induction action by the genes.

With the proviso that the calculated or speculated sum activity of the expression induction activities exerted by IFN-$\alpha$2 and IFN-$\alpha$8 subtypes each alone is expressed as a level 1, the expression enhancer of the present invention usually exerts a synergistic action with a level of at least 1.2 times, and preferably a level of at least 1.5 times greater expression induction action. The synergism can be confirmed, for example, by multivariate analysis as disclosed by T. C. Chou, "Synergism and Antagonism in Chemotherapy", pp. 61–102 (1991), published by Academic Press. According to the method, the presence of synergism and the level of two different types of medicaments can be numerated as a combination index (CI) for evaluation as shown in Table 2. Depending on genes to be tested, CI of the expression enhancer of the present invention is usually less than 0.9, preferably, less than 0.85.

TABLE 2

| CI | Evaluation | Symbol |
| --- | --- | --- |
| 0.1–0.3 | Strong synergism | + + + + |
| 0.3–0.7 | Synergism | + + + |
| 0.7–0.85 | Moderate synergism | + + |
| 0.85–0.90 | Slight synergism | + |
| 0.90–1.10 | Roughly additive action | ± |
| 1.10–1.20 | Slight negative synergism | – |
| 1.20–1.45 | Moderate negative synergism | – – |
| 1.45–3.3 | Negative synergism | – – – |

The activity ratio of IFN-$\alpha$2 and IFN-$\alpha$8 subtypes in the expression enhancer of the present invention is not specifically restricted to as long as such a synergism against at least one protein synthesis inhibitory gene is exerted. Varied depending on the kinds/types of genes and cells to be applied, the desired synergism is most clearly exerted when the activity ratio is adjusted to at least 1:0.25 but less than 1:1.5 in terms of international unit. In addition, when a preferable ratio of IFN-$\alpha$2 and IFN-$\alpha$8 subtypes to be incorporated into the expression enhancer of the present invention in order to clearly exert the desired synergism, it is usually adjusted to at least 1:0.05 but less than 1:0.5, preferably, at least 1:0.06 but less than 1:0.4 by weight ratio, depending on the purification degree of and the preparation method for subtypes used. The weight of subtypes as referred to as in the present invention means the weight, corresponding to that of polypeptide chains, quantified by subjecting them in an isolated form to conventional quantitation methods for proteins such as the Lowry method and the ultraviolet absorption method using as a standard specimen a simple protein substantially free of saccharide chain.

Within the range of not diminishing the synergism of IFN-$\alpha$2 and IFN-$\alpha$8 subtypes, other subtypes of IFN-$\alpha$ can be added to the expression enhancer of the present invention. For example, since IFN-$\alpha$1 and IFN-$\alpha$7 subtypes usually do not substantially affect the synergism of IFN-$\alpha$2 and IFN-$\alpha$8 subtypes when used in a relatively lesser amount, they can be incorporation into the expression enhancer. Varied depending on the kind/types of genes and cells to be applied, the expression enhancer, which usually contains IFN-$\alpha$2 and IFN-α8 subtypes in an amount of at least 90%, preferably, at least 95%, and more preferably, at least 98% to the total amount of IFN-α in terms of international units, has a character of exerting a relatively clear synergism in the induction of gene expression, independently of subtypes contained therein other than the IFN-α2 and IFN-α8 subtypes.

In the expression enhancer of the present invention, the activity ratio of IFN-α2 and IFN-α8 subtypes and the percentage of the total activity thereof to that of IFN-α can be determined as follows: Firstly, the expression enhancer is purified into a form consisting essentially of IFN-α subtypes using, for example, a column of anti-human IFN-α antibody. Thereafter, the purified specimen is fractionated by conventional methods such as ion-exchange chromatography and reverse-phase chromatography for separating and isolating IFN-α subtypes into each IFN-α subtype. If necessary, the isolated IFN-α subtypes are confirmed what IFN-α subtypes they are by the N-terminal amino acid sequence analysis, etc. According to the method defined in the present invention, the specific activity (IU/mg protein) of the isolated each subtype is determined. The purified IFN-α specimen obtained in the above is analyzed, for example, on high-performance liquid chromatography for separation into each IFN-α subtype. Based on the ratio of the peak areas of the data on a chromatogram the weight ratio of IFN-α2 and IFN-α8 subtypes to the total amount of IFN-α is determined, using the specific activity and the ratio of IFN-α2 and IFN-α8 subtypes thus obtained, the aimed activity ratio can be calculated in terms of international units.

The expression enhancer of the present invention can be prepared by various methods. Natural IFN-α2 and IFN-α8 subtypes are preparable by allowing human cells to produce IFN-α and collecting the produced IFN-α2 and IFN-α8 subtypes from the resulting product. Using the subtypes thus obtained, the enhancer of the present invention can be prepared. As the human cells used in the above preparation, two or more different types of cells can be used in an appropriate combination depending on their IFN-α productivity as long as they produce either or both of IFN-α2 and IFN-α8 subtypes when stimulated with appropriate inducers. Examples of such cells include macrophages and white blood cells such as lymphocytes and monocytes, which are isolated from living human bodies; and cell lines established from humans such as human lymphoblastoid cells. Since BALL-1 cells, a human lymphoblastoid cell, disclosed by S. Hiraki in "*Journal of National Cancer Institute*", Vol. 59, p. 93 (1977), satisfactorily produce the above-mentioned subtypes, they can be particularly useful in the present invention. To produce IFN-α from the above cells, they are allowed, to proliferate in vitro or within the body of warm-blooded animals excluding humans. The methods for in vitro proliferation include conventional ones for culturing animal cells using culturing wares, jar fermentors, etc., and those for in vivo proliferation include conventional ones which use living bodies such as mammals including hamsters, normal mice, nude mice, rats, guinea pigs, rabbits, horses, pigs, goats, monkeys, cats, and dogs; and poultry including hens and pigeons, as disclosed, for example, in Japanese Patent Kokoku No. 54,158/81. Thereafter, IFN-α can be produced by allowing IFN inducers to act on the above cells at an appropriate timing during, before, or after the cell proliferation in vivo or in vitro. Examples of the IFN inducers are viruses, double-stranded RNAs, microorganisms, endotoxins, and cytokines capable of inducing the expression of IFN-α such as IFN-α per se, IL-1 and TNF.

Consequently, IFN-α or either or both of IFN-α2 and IFN-α8 subtypes of IFN-α are collected from the products obtained in the above procedures for preparing IFN-α. The methods for collecting IFN-α include conventional ones in general, for example, salting out, dialysis, filtration, centrifugation, concentration, lyophilization, gel filtration chromatography, ion-exchange chromatography, affinity chromatography, reverse-phase chromatography, isoelectric point fractionation, and electrophoresis. Specimens of IFN-α, purified to the desired level, can be obtained by appropriately combining the above conventional methods to effect fractionation and collecting from the resulting fractions the desired fractions, for example, those with the desired anti-virus activity. More particularly, the products in the above procedures for producing IFN-α are firstly fractionated on chromatography such as affinity chromatography using anti-IFN-α antibodies as carriers to obtain purified IFN-α specimens substantially free of concomitant proteins other than IFN-α, and then the specimens are fractionated by ion-exchange column chromatography, reverse chromatography, etc., to separate into each subtype. Thus, an electrophoretically, substantially homogeneously purified specimen of IFN-α2 or IFN-α8 subtype can be obtained. If necessary, these purified subtypes can be further concentrated, dried, etc., and then mixed in the desired activity ratio; or, if needed, one or more of the later described recombinant IFN-α subtypes and other subtypes modified with water-soluble macromolecules can be used in combination to give the desired activity ratio of IFN-α2 and IFN-α8 subtypes for use as the effective ingredients of the expression enhancer of the present invention. During the steps for collecting IFN-α, any specimen can be used as the effective ingredient of the expression enhancer of the present invention as long as it has an activity ratio of IFN-α2 and IFN-α8 subtypes within the desired range and has a purity of at least a level that does not hinder the object of the present invention. In addition, specimens of IFN-α2 and IFN-α8 subtypes, which can be isolated similarly as above from an IFN-α specimen commercialized by Cosmo Bio Co., Ltd., Tokyo, Japan, can be used as the effective ingredients of the expression enhancer of the present invention; and when the activity ratio and the purity of IFN-α2 and IFN-α8 subtypes in the specimens have an activity ratio and a purification level which both reach the desired levels, they can be used intact as the effective ingredient of the expression enhancer of the present invention.

To prepare the expression enhancer of the present invention by using the recombinant DNA technology, DNAs encoding the desired subtypes are firstly prepared with reference to conventional information. For example, M. O. Diaz et al., in "*Journal of Interferon and cytokine Research*", Vol. 16, No. 2, pp. 179–180 (1996) tabulated literatures which report DNAs encoding human IFN-α subtypes. Commonly available databases for nucleic acids are also useful; the nucleotide sequences, registered for GenBank under the accession codes "J00207" and "X03125", are the DNAs which encode IFN-α2 and IFN-α8 subtypes and are respectively shown in SEQ ID NOs: 3 and 4 in the present specification. Based on these information, the desired DNAs can be obtained by applying commonly used methods for cloning DNAs such as PCR to RNAs or DNAs obtained from appropriate sources. Secondary, the DNAs thus obtained are inserted into appropriate expression vectors. Examples of such vectors used in the present invention include plasmid vectors such as pET, pKK223-3, pcDNAI/Amp, BCMGSNeo, pcDL-SRα, pKY4, pSV2-neo, pSV-2gpt, pCDM8, pCEV4, pME18S, and pEF-BOS. The replicable vectors usable in the present invention usually contain appropriate nucleotide sequences, which are needed for expressing the DNAs of the present invention in host cells, such as promotors, enhancers, replication origins, transcription termination sites, splicing sequences, and/or selective sequences. When used, as promoters, heat shock protein promoters and another promoters as disclosed in Japanese Patent Kokai No. 163,368/95 applied for by the same applicant as the present invention, the expression of the above DNAs in transformants can be artificially controlled by external stimuli.

The recombinant DNAs thus obtained are then inserted into appropriate hosts. Examples of such hosts are microorganisms including commonly used appropriate procaryotic and eucaryotic cells; other cells derived from plants and animals such as vertebrate and invertebrate animals, and plant- and animal-bodies in themselves. Practical examples of such animal host cells are epithelial-, interstitial-, and hemopojetic-cells derived from humans, monkeys, mice and hamsters including 3T3-Swiss albino cells (ATCC CCL-92), C1271 cells (ATCC CRL-1616), CHO-K1 cells (ATCC CCL-61), CV-1 cells (ATCC CCL-70), COS-1 cells (ATCC CRL-1650), HeLa cells (ATCC CCL-2), MOP-8 cells (ATCC CRL-1709), and mutants thereof. To introduce the DNAs of the present invention into the above hosts, for example, the following methods can be used; conventional DEAE-dextran method, calcium phosphate transfection, electroporation, lipofection, microinjection, and virus-infection methods using viruses such as retro virus, adeno virus, herpes virus, and vaccinia virus. Among the resulting transformants, the desired clone capable of producing the desired subtype(s) can be selected. After culturing the selected clone in an appropriate medium, the proliferated clones are allowed to produce IFN-α optionally in the presence of an appropriate IFN-α inducer, followed by purifying the products in the culture either by the methods similarly as used in the preparation of natural IFN-α2 and IFN-α8 subtypes as in the above or according to conventional methods suitable for the system of hosts and vectors used to obtain recombinant IFN-α2 and IFN-α8 subtypes. Thereafter, both subtypes can be mixed in the desired activity ratio, or, if necessary, they can be combined with one or more of the above natural subtypes and the later described subtypes modified with water-soluble macromolecules to give the desired activity ratio of IFN-α2 and IFN-α8 subtypes. Thus, the effective ingredients of the expression enhancer of the present invention can be obtained.

To prepare the modified IFN-α2 and IFN-α8 subtypes with water-soluble macromolecules, the desired natural or recombinant subtypes are firstly prepared by any of the above methods, and then subjected to conventional reactions for covalently binding water-soluble macromolecules to the resulting subtypes. The term "water-soluble macromolecules" as referred to as in the present invention usually means substances, which are composed of a repeating unit of the same or different monomers and have a molecular weight of at least 500 and satisfactory solubility in water, and which include natural and synthetic molecules, as well as their partial hydrolyzates and modified products. Examples of such are soluble starches, amylopectins, dextrans, polysucroses, pullulans, elsinans, curdrans, gum arabics, tragacanth gums, guar gums, xanthan gums, carrageenans, hyaluronic acid, heparin, glucomannans, chitosans, lipopolysaccharides, polyethylene glycols, polyvinyl pyrrolidone, asialo orosomucoids, asialofetuin, albumins, galactose-modifiedalbumins, polylysines, andgalactose-modified polylysines. The molecular weight of the macromolecules preferably usable in the present invention is usually 500–10,000,000, preferably, 10,000–1,000,000 as an average molecular weight, depending on the types/kinds of the water-soluble macromolecules used.

To covalently bind the above water-soluble macromolecules to IFN-α2 and/or IFN-α8 subtypes, conventional methods such as diazo, peptide, alkylation, cross-linking, and amido-binding methods can be used. Representative examples thereof are described in detail, for example, in Japanese Patent Kokai No. 93,730,91 and Japanese Patent No. 1,162,778, applied for by the same applicant as the present invention. These methods can be also advantageously used in the present invention. In addition, conventional methods for covalently binding water-soluble macromolecules to the desired proteins using the action of transglutaminase can be advantageously used. For example, international Publication No. WO 96/10089 discloses a method using the action of transglutaminase.

To obtain the modified products using the diazo method, IFN-α2 and/or IFN-α8 subtypes can be reacted with derivatives of water-soluble macromolecules, which are prepared by introducing into intact water-soluble macromolecules aromatic amino groups such as p-aminobenzyl group, p-aminobenzoyl group, m-aminoanisole group, m-aminobenzyloxymethyl group, 3-(p-aminophenoxy)-2-hydroxypropionyl group, and 3-(p-amino-m-methylanilino)-5-chlorotriazinyl group.

To obtain the modified products using the peptide method, IFN-α2 and/or IFN-α8 subtypes can be reacted with activated derivatives of water-soluble macromolecules, which have been activated by providing either water-soluble macromolecules having carboxylate group per se or carboxylated water-soluble macromolecules, and then either making the macromolecules by conventional methods into carboxylic acid derivatives thereof such as acid azides, acid chlorides, carbodiimide, and isocyanates, or reacting the macromolecules having carboxylic acid per se with cyanuric acid halides into water-soluble macromolecules activated by cyanuric acid halides.

To obtain the modified products using the alkylation method, for example, IFN-α2 and/or IFN-α8 subtypes can be reacted with halogenated alkyl derivatives of water-soluble macromolecules obtainable by introducing into appropriate water-soluble macromolecules chloroacetyl group, bromo acetyl group, iodine acetyl group, or triazinyl halide group.

To obtain the modified products using the cross-linking method, for example, IFN-α2 and/or IFN-α8 subtypes can be reacted with water-soluble macromolecules in the presence of cross-linking reagents such as glutaraldehyde, glyoxal, succinaldehyde, hexamethylene diisocyanate, toluene-2,4-diisocyanate, bis-azobenzidine, and N,N'-ethylene-bis-maleineimide.

To obtain modified products by the amido-binding method, for example, IFN-α2 and/or IFN-α8 subtypes can be reacted with activated water-soluble macromolecules, which are obtainable by reacting either water-soluble macromolecules having amino groups per se or aminated water-soluble macromolecules with haloacylhalides such as bromoacetylbromide, chlorobutylchloride, fluoropropionylfluoride, and iodovaleryliodide.

To obtain modified products by the action of transglutaminase (EC 2.3.2.13), IFN-α2 and/or IFN-α8 subtypes can be reacted with either water-soluble macromolecules having either amino groups per se or aminated water-soluble macromolecules in the presence of transglutaminase from an appropriate origin. Any reaction conditions can be used in the present invention as long as they do not hinder the acyl-transferring reaction between primary amines and γ-carboxyamido groups of glutamine residues of proteins. As transglutaminase, those derived from microorganisms, particularly, those from microorganisms of the genus Actinomycetes can be advantageously used to prepare the modified products in practicing the present invention because they have relatively high thermal and pH stabilities than those from other origins.

Depending on the reaction methods used, the ratio or IFN-α2 or IFN-α8 subtype to a water-soluble macromolecule is usually selected from the range of from 1:0.001 to 1:1,000, preferably, from 1:0.01 to 1:100. Ratios of far below the above range are not preferable because, in some reaction methods, IFNα2 or IFN-α8 subtype in itself may strongly bind together, while ratios far over the above range are not preferable because water-soluble macromolecules in themselves may bind together. Any reaction temperature, pH, and time can be used in the present invention as long as they neither inactivate nor decompose IFN-α2 and IFN-α8 subtypes but inhibit undesirable side reactions as much as possible; usually, these conditions are preferably set to temperatures from 0 to 100° C., pHs from about 1 to about 12, and times from 0.1 to 50 hours. For example, depending on use of the modified products of IFN-α2 and IFN-α8 subtypes, when specific modifications of the subtypes by water-soluble macromolecules having characteristic features are required with respect to their average molecular weights and molecular weight distributions, it is preferable to use water-soluble macromolecules having such characteristic features to meet the object for their preparations. Among commercialized products of water-soluble macromolecules, there are products with a specifically controlled average molecular weight and molecular weight distribution, and therefore suitable ones can be selected thereamong as materials to meet the object. As disclosed in Japanese Patent Kokai No. 65,302/94 and Japanese Patent No. 866,889, which were applied for by the same applicant as the present invention, the methods of producing pullulan having the desired average molecular weights and molecular weight distributions, while controlling the culture conditions of microorganisms capable of producing pullulan, are useful in preparing the materials for the modified products usable in the present invention. Among the aforesaid modified products of IFN-α2 and/or IFN-α8 subtypes, those modified with polysaccharides such as puilulan and elsinan consisting essentially of a repeating unit of maltotriose, preferably, those which have a molecular weight of 10,000–1,000,000 are examples of the particularly advantageously useful ones usable in the present invention with respect to their relatively high stability in humans in vitro and relatively lesser antigenicity to humans in vitro.

The modified products of IFN-α2 and IFN-α8 subtypes, prepared by the above reaction methods, can be made into specimens purified up to the desired level through the purification procedures according to those for natural or recombinant IFN-α2 and IFN-α8 subtypes. The resulting modified products of IFN-α2 and IFN-α8 subtypes can be mixed in the desired activity ratios and optionally mixed in combination with one or more other natural and recombinant subtypes to give the desired activity ratios of IFN-α2 and IFN-α8 subtypes.

As an expression enhancer for protein synthesis inhibitory genes usable in a variety of fields, the composition comprising IFN-α2 and IFN-α8 subtypes thus obtained can be used alone or after mixed with appropriate another ingredients such as carriers, buffers, stabilizers, solvents, and diluents depending on use. For example, the expression enhancer of the present invention induces the expression of protein synthesis inhibitory genes in humans in vivo to greatly exert an inhibitory effect on cell abnormality. Also the expression enhancer can be arbitrarily used as an effective ingredient in pharmaceutical compositions because IFN-α2 and IFN-α8 subtypes are widely used in medical uses directed to humans. Depending on the symptoms of diseases and uses to be applied, the pharmaceutical compositions according to the present invention can be provided as those in the form of a liquid, solid or semi-solid, which comprise the expression enhancer of the present invention as an effective ingredient and another commonly used physiologically acceptable ingredient(s), i.e., carriers, excipients, stabilizers, solvents, and buffers, and optionally one or more physiologically active substances which are usually used in a pharmaceutical field. The above stabilizers used in the present invention include proteins such as serum albumin and gelatin, and saccharides such as glucose, sucrose, lactose, maltose, trehalose, sorbitol, maltitol, mannitol, and lactitol. The above buffers include those which are mainly composed of citrates or phosphates. Further, the above physiologically active substances include nitrogen mustard N-oxide hydrochloride, mercaptopurine, etoposide, actinomycin D, mitoxanthrone hydrochloride, L-asparaginase, lentinan, acyclovir, and cytokines such as IL-1, TNF, and IFN-γ.

The pharmaceutical compositions thus obtained can be used as medicaments for treating, relaxing or preventing diseases such as those in immune system, hematopoietic tissues, circulatory organs, dermatological tissues, digestive organs, nervous system, muscles, and eyes; more particularly, allergies, rheumatism, AIDS, leukemia, malignant melanoma, sarcoma, conjunctivitis, hepatitis, and enterocolitis, whose symptoms can be treated, relieved or prevented by direct or indirect correlation with protein synthesis inhibitory genes. Depending on diseases to be treated, the administration route is selected from intravenous, intramuscular, subcutaneous, intradermal, intraperitoneal, percutaneous, and oral administrations. Although the dose of the pharmaceutical compositions are varied depending on patients' ages, types and symptoms of diseases to be treated, and administration routes, the compositions, when injected intramuscularly, are usually administered to patients successive days or at an interval of one or two days or more at a dose of one to ten millions IU, preferably, three to six millions IU, in terms of international units, of the total amount of the effective ingredients per adult per day while observing the patients' symptoms. When orally administered, the pharmaceutical compositions are usually administered to patients successive days or at an interval of one or two days or more at a dose of 10–2,000 IU, preferably, 20–800 IU, and more preferably, 40–400 IU while observing the patients' symptoms.

The fact that the expression enhancer of the present invention more strictly induces the expression of protein synthesis inhibitory genes as compared with a single use of IFN-α2 or IFN-α8 subtype means that it enables more clear observation of intracellular reactions when allowed to act on IFN-α sensitive cells. Accordingly, the expression enhancer can be advantageously used as a research reagent for molecular analysis of intracellular molecular function, for example, intracellular signal transduction system which participates in the action of IFN-α on its sensitive cells to induce the expression of protein synthesis inhibitory genes.

The synergism of the expression enhancer of the present invention entirely depends on the structure of a transcriptional regulatory region of a gene concerned by the expression enhancer but does not usually influence on the gene expression product per se. Based on this, the desired proteins can be effectively expressed in cells in such a manner of isolating a transcriptional regulatory region of a gene concerned by the expression enhancer, and then providing a recombinant DNA into which the gene or the structural gene that encodes the desired protein controlled by the region has been inserted, introducing the recombinant DNA into IFN-α sensitive cells, and stimulating the cells with the expression enhancer. As the IFN-α sensitive cells, human cells which inherently express human IFN-α receptors on their cell surface and other human or non-human vertebrate animal cells which are constructed to express human IFN-α receptors on their cell surface by the recombinant DNA technology can be used. The proteins to be expressed may be those of human origin or others, for example, non-human vertebrate animal, non-vertebrate animal, plant, and microorganism origins. Accordingly, the expression enhancer of the present invention can be arbitrarily used as an inducer for producing recombinant proteins.

As described above, IFN-α2 and IFN-α8 subtypes exert a synergism in inducing protein synthesis inhibitory genes so that IFN-α2 subtype can be used to enhance the induction action on the expression of protein synthesis inhibitory genes by IFN-α8 and vice versa. Based on this fact, the present invention provides an expression enhancer for gene expression comprising IFN-α2 and/or IFN-α8 subtypes as an effective ingredient(s) and provides a method of enhancing the expression of such a gene by using either or both of the subtypes. The expression enhancer and the method according to the present invention can be arbitrarily used in the fields of medicine, research reagents, and protein productions to which the expression enhancer is applicable.

The construction of the expression enhancer as disclosed in the present invention can be applicable to gene therapy: According to conventional gene therapy, DNAs encoding IFN-α2 and IFN-α8 subtypes can be either inserted into vectors from viruses such as retrovirus, adenoViruS, and adeno-associated virus; or embedded in liposomes such as catioflic polymers and membrane fusion-type liposomes after being linked to other nucleotide sequences, and, if necessary, further directly injected into patients suffering from diseases susceptive to the expression of protein synthesis inhibitory genes. Alternatively, after being inserted into appropriate vectors, the above DNAs can be introduced in vitro into lymphocytes collected from the patients, and the resulting lymphocytes are self-implanted into the patients. DNAs encoding either of the subtypes can be arbitrarily manipulated to be located in the downstream of transcription regulatory regions with different transcription activities to control the expression level of each subtype. As a result, the above-exemplified diseases can be treated/relieved because of the coexistence of IFN-α2 and IFN-α8 subtypes induced in patients who were received with such gene therapies. General procedures of practicing the above gene therapies per se are disclosed in detail, for example, in "Jikken-Igaku-Bessatsu-Biomanual-UP-Series, *Basic techniques for Gene Therapy*", edited by Takashi Shimada, Izumi Saito, and Keiya Ozawa, published by Yodo Sha, Tokyo, Japan (1996).

The following Experiments and Examples disclose the present invention in more detail:

Experiment 1: Synergism of IFN-α2 and IFN-α8 Subtypes in Inducing the Expression of Protein Synthesis Inhibitory Genes Experiment 1-1: Preparation of IFN-α2 and IFN-α8 Subtypes Experiment 1-1(a): Preparation of Transformant Capable of Producing IFN-α Subtype Information for a nucleotide sequence. of an IFN-α2 subtype gene, registered for GenBank, a nucleotide database, under the accession code "J00207", was obtained therefrom. The nucleotide sequence is in SEQ ID NO: 3. Using both a primer constructed based on the information and a human chromosome DNA as a template, a DNA fragment containing a nucleotide sequence corresponding to a mature-type IFN-α2 subtype, which had nucleotide residues 580 to 1077 of SEQ ID NO:3 and in which an initiation codon had been added to the 5'-terminus by conventional PCR, was amplified. According to conventional manner, the resulting amplified DNA fragment was inserted into the downstream of a promotor "pET-3a", an expression vector commercialized by Toyobo Co., Ltd., Tokyo, Japan. Thus, an IFN-α2 subtype expression plasmid was prepared. The plasmid was in a usual manner inserted into "BL21 (DE3)", an *Escherichia coli* competent cell commercialized by Toyobo Co., Ltd., Tokyo, Japan, to obtain a transformant capable of producing IFN-α2 subtype.

Information for a nucleotide sequence of an IFN-α8 subtype gene, registered for GenBank, a nucleotide database, under the accession code "X03125", was obtained. The nucleotide sequence is in SEQ ID NO:4. Using both a primer constructed based on the information and a human chromosome DNA as a template, a DNA fragment containing a nucleotide sequence corresponding to a mature-type IFN-α8 subtype, which had nucleotide residues 117 to 614 of SEQ ID NO:4 and in which an initiation codon had been added to the 5'-terminus by conventional PCR, was amplified. According to conventional method the resulting amplified DNA fragment was inserted into the downstream of a promotor "pET-3a", an expression vector commercialized by Toyobo Co., Ltd., Tokyo, Japan. Thus, an IFN-α8 expression plasmid was obtained. The plasmid was in a usual manner inserted into "BL21 (DE3)", an *Escherichia coli* competent cell commercialized by Toyobo Co., Ltd., Tokyo, Japan, to obtain a transformant capable of producing IFN-α8 subtype.

Experiment 1-1(b): Production and Purification of IFN-α Subtype

Each transformant in Experiment 1-1(a) was in a usual manner cultured with both L-broth as a nutrient culture medium and isopropyl-β-D-thiogalactopyranoside (IPTG) as an inducer to intracellularly produce each subtype. The resulting cells were collected by centrifuging each culture, suspended in PBS, and ultrasonically disrupted. Each of the cell disruptants was centrifuged to collect a supernatant. Using hydrophobic chromatography, ion-exchange chromatography, and gel filtration chromatography, the collected supernatants were respectively fractionated in a usual manner to purify fractions with anti-virus activity. According to conventional manner, a portion of a purified fraction was subjected to SDS polyacrylamide gel electrophoresis (SDS-PAGE) under reducing conditions, revealing that the purified fraction for each subtype was confirmed to be a substantially, electrophoretically single protein band.

A portion of each fraction of each transformant, purified on gel filtration chromatography, was sampled and subjected in a usual manner to the Edman degradation method after being treated with reducing carboximidemethyl to decode an amino acid sequence from the N-terminus to the amino acid residue 30. The purified fraction obtained from the transformant capable of producing IFN-α2 subtype had a methionine residue at the N-terminus, and the resulting sequence completely coincided with the amino acid sequence of IFN-α2 subtype as shown in SEQ ID NO:1, a signal peptide-free N-terminal amino acid sequence of amino acid residues 24 to 52, registered for SWISSPROT under the primary accession number P01563. While in the case of the transformant capable of producing IFN-α8 subtype, it had methionine at the N-terminus, and the resulting sequence completely coincided with the amino acid sequence of IFN-α8 subtype as shown in SEQ ID NO: 2, a signal peptide-free N-terminal amino acid sequence of amino acid residues 24 to 52, registered for SWISSPROT under the primary accession number P32881. Based on these data, it was confirmed that the two purified specimens, having an electrophoretically single protein band obtained in this experiment, were respectively purified specimens of IFN-α2 and IFN-α8 subtypes.

Experiment 1-1(c): Specific Activity

According to the dye uptake method as disclosed by J. Imanishi in "Biken Journal", Vol. 24, pp. 108–109, the inhibitory action of IFN-α samples on cytopathic effect (CPE) by Sindbis virus against FL cells, an established cell line derived from human amnion cell, was quantified by measuring the amount of a dye taken up by normal cells at a wavelength of 540 nm using a neutral red as the dye: The 50% inhibitory dilution rate for CPE was determined by using dilutions of the purified specimen of IFN-α2 subtype in Experiment 1-1(b) as an IFN-α specimen diluted stepwisely by two times in series, and by using dilutions of "Ga23-901-532", an international standard specimen of IFN-α with 25,000 IU/ample, obtained from the National Institutes of Health (NIH), diluted stepwisely by two times in series. Based on the data, the anti-virus activity (IU/ml) of the purified specimen of IFN-α2 subtype in Experiment 1–1(b) was calculated. Alternatively, the protein content of the purified specimen of IFN-α2 subtype in Experiment 1-1(b) was assayed by the Lowry method. Based on these data, the purified specimen of IFN-α2 subtype in Experiment 1-1(b) was calculated at $7.2 \times 10^7$ IU/mg protein, and the purified specimen of IFN-α8 subtype in Experiment 1-1(b) was calculated at $3.0 \times 10^8$ IU/mg protein.

Experiment 1-2: Synergism of IFN-α2 and IFN-α8 Subtypes in Inducing the Expression of Protein Synthesis Inhibitory Gene HepG2 cells (ATCC HB-8065), an established cell line from human liver cell, were cultured in a usual manner in RPMI 1640 medium containing 10% (v/v) fetal calf serum until reaching the prescribed cell number, and then prepared into a cell suspension with a cell density of $1 \times 10^5$ cells/ml using a fresh preparation of the same medium as above. The cell suspension was injected into a 96-well microplate in a volume of 100 μl/well and incubated in a 5% (v/v) $CO_2$ incubator at 37° C. for 48 hours.

Using the purified specimens in Experiment 1-1(b), there were provided solutions of mixtures of IFN-α2 and IFN-α8 subtypes, which contained IFN-α2 and IFN-α8 subtypes in activity ratios of 10:0, 8:2, 6:4, 5:5, 4:6, 2:8 and 0:10 in terms of international units, and had a calculated total IFN-α activity Of $1 \times 10^4$ IU/ml. Each of the solutions was stepwisely diluted two times in series using a fresh preparation of the same medium as above. Based on their specific activities obtained in Experiment 1-1(c), the weight ratios of IFN-α2 and IFN-α8 subtypes in the mixture solutions in this experiment were calculated at 100:0, 94:6, 86:14, 81:19, 74:26, 51:49, and 0:100.

To each well in the microplate containing HepG2 cells after the 48-hour culture was added a stepwisely diluted solution of IFN-α2 and IFN-α8 subtypes having each of the above activity ratios in a volume of 50 μl/well, and the solution in each well was sufficiently mixed, followed by continuing to culture the cells for additional 24 hours.

Thereafter, the resulting culture supernatant was removed from each well, and then a previously prepared VSV (vesicular stomatitis virus) solution having a virus density of $3 \times 10^5$ pfu/ml was poured into each well in a volume of 100 μl/well, followed by further culturing the cells for 24 hours. As a control, there was provided a system free of the treatment of IFN-α and VSV, followed by initiating cell culture from the same initial cell density per well as above and then continuing the culturing for the same period of time as above. All the culture systems were respectively provided similarly in a triplicate manner.

After completion of the culture, the cells were collected from each well and counted for viable cells in a usual manner, followed by calculating a mean value for each system. Based on these results, a viability curve for HepG2 cells in the system with each solution of IFN-α2 and IFN-α8 subtypes was drawn by plotting the number of viable cells corresponding to the dilution rate of each solution. A mean value of a concentration, that showed a 50% inhibitory effect on CPE by VSV against HepG2 cells, i.e., $IC_{50}$, a total IFN-α activity per milliliter (IU/ml) on a calculatione, was calculated based on the dilution rate that retained a 50% viability of HepG2 cells of that of control with respect to each viability curve for each mixture solution of IFN-α2 or IFN-α8 subtype. The calculated values were analyzed on the multivariate analysis as disclosed by T. C. Chou, "Synergism and Antagonism in Chemotherapy", pp. 61–102 (1991), published by Academic Press, and then the presence of and the level of the synergism by IFN-α2 and IFN-α8 subtypes were numerated as a combination index (CI). The levels of CI are tabulated in the aforesaid Table 2. The results are in Table 3.

TABLE 3

| Activity ratio of | Anti-virus activity | Evaluation of synergism | |
| --- | --- | --- | --- |
| IFN-α2:IFN-α8 | ($IC_{50}$, IU/ml) | CI | Symbol |
| 10:0 | 512 | | |
| 8:2 | 318 | 0.99 | ± |
| 6:4 | 285 | 0.90 | + |
| 5:5 | 241 | 0.73 | + + |
| 4:6 | 254 | 0.94 | ± |
| 2:8 | 231 | 1.06 | ± |
| 0:10 | 210 | | |

As is evident from Table 3, particularly, from the results in the activity ratio of 10:0 and 0:10, it was revealed that, in the system that VSV exhibited CPE on HepG2 cells, IFN-α8 exerted a greater anti-virus activity, e.g., about 2.4-times greater anti-virus activity than that of IFN-α2 as compared with their $IC_{50}$, when either of IFN-α2 and IFN-α8 subtypes was added alone to the system. From the data, it might be speculated that $IC_{50}$ gradually decreases and ends to a value of that of 0:10, with the proviso that IFN-α2 and IFN-α8 subtypes exhibit only an arithmetic anti-virus activity in the systems with solutions prepared by mixing the subtypes in such a manner by allowing the percentage of IFN-α8 subtype to be increased by stepwisely changing the ratio of IFN-α2 and IFN-α8 subtypes. However, at around the data on the mixture solutions of IFN-α2 and IFN-α8 subtypes with an activity ratio of 5:5 (=IFN-α2:IFN-α8), the calculated $IC_{50}$ resulted to show opposite values to the above speculation, and this led to an estimation that the subtypes show a synergism when mixed in a particular ratio. This was evidenced by the multivariate analysis of $IC_{50}$ as in the right column in Table 3 and revealed that the subtypes show a particularly high synergism when used in an activity ratio of from 6:4 to 5:5 (=IFN-α2:IFN-α8).

As evident from the above results, IFN-α2 and IFN-α8 subtypes exert a distinct synergism when mixed in a prescribed ratio in expressing anti-virus activity. The fact means that, when mixed in such an activity ratio, the subtypes exert a distinct synergism in inducing the expression of protein synthesis inhibitory genes such as 2–5A synthetase gene and PKR gene, which are the genes for encoding functional molecules participating directly in anti-virus activity.

Using recombinant IFN-α1, IFN-α5 and IFN-α10 subtypes which had been prepared in accordance with the above procedures, their effects were examined when used in combination with IFN-α8 subtype, revealing that the combination use of IFN-α8 subtype with IFN-α5 or IFN-α10 subtype showed no synergism, and depending on their activity ratios, there was found an apparently negative synergism in some cases. In the case of combining IFN-α1 subtype with IFN-α8 subtype, a slight synergism was occasionally found but was not so high as in the case of combining IFN-α2 subtype with IFN-α8 subtype. These results show that the combination of IFN-α2 and IFN-α8 subtypes particularly, outstandingly enhances the expression of protein synthesis inhibitory genes.

Experiment 2: Synergism of IFN-α2 and IFN-α8 Subtypes in Inducing the Expression of 2–5A Synthetase Gene HepG2 cells (ATCC HB-8065), an established cell line from human liver cell, were cultured in a usual manner in RPMI 1640 medium containing 10% (v/v) fetal calf serum until reaching the prescribed cell number, and then prepared into a cell suspension with a cell density of $1 \times 10^5$ cells/mi using a fresh preparation of the same medium as above. The cell suspension was injected into a 24-well microplate in a volume of one milliliter per well and incubated in a 5% (v/v) $CO_2$ incubator at 37° C. for 48 hours.

Using the purified specimens in Experiment 1-1(b), there were provided mixture solutions of IFN-α2 and IFN-α8 subtypes, which contained the subtypes in activity ratios of 10:0, 8:2, 6:4, 5:5, 4:6, 2:8 and 0:10 (=IFN-α2:IFN-α8) in terms of international unit, and had a calculated total IFN-α activity of 200 IU/ml.

Twenty-five micromilliliters of either of the mixture solutions were added to each well with HepG2 cells after the 48-hour culture in each microplate, and the solution in each well was sufficiently mixed, followed by continuing to culture the cells for additional 24 hours. As a control, there was provided a system free of IFN-α treatment and started culturing cells from the same initial cell density per well as above and continued culturing the cells for the same period of time as above. All the culture systems were respectively provided similarly in a triplicate manner.

After completion of the culture, the cells in each well were collected therefrom, suspended respectively in PBS, and extracted by freezing and thawing to obtain a 100 μl cell extract. The 2–5A synthetase activity in each cell extract was assayed as 2–5A amount (pmol/dl) formed by the action of 2–5A synthetase using "2–5A KIT EIKEN", a commercialized kit for assaying 2–5A synthetase, produced by Eiken Chemical Co., Ltd., Tokyo, Japan, followed by calculating the mean value for each system. The value calculated from a mean value of a system with an IFN-α subtype minus that of control system was evaluated as 2–5A synthetase induction activity for each sample. In the case of using a ratio of 10:0 with only an IFN-α2 treatment, the value was about 200 pmol/dl; while in the case of using a ratio of 0:10 with only the IFN-α8 treatment, the value was about 450 pmol/dl. Thus, a good correlation between the differences of anti-virus activities of both subtypes, observed in Experiment 1-2, was found.

As the data is not shown, the results from a preliminary experiment resulted in a finding that there was a linear relationship between the logarithmic value (the base 10) of the anti-virus activity ($IC_{50}$), obtained by the method in Experiment 1-2, and the value (pmol/dl) of the 2–5A synthetase induction activity measured under the conditions in this experiment. Based on this finding, the presence of synergism was judged by determining the magnification of the value measured in this experiment to that of the 2–5A synthetase induction activity (pmol/dl), with the proviso that IFN-α2 and IFN-α8 subtypes acted synergistically. The results are in Table 4.

TABLE 4

| IFN-α2:IFN-α8 (activity ratio) | Judgement* of synergism in inducing 2-5A synthetase |
|---|---|
| 8:2 | + |
| 6:4 | + + |
| 5:5 | + + |
| 4:6 | ± |
| 2:8 | ± |

The symbol "*" means the judgement based on the magnification of the value measured to that of the 2-5A synthetase induction activity (pmol/dl), with the proviso that IFN-α2 and IFN-α8 subtypes acted synergistically. The symbol "±" means a magnification of at least 0.9 but below 1.2; "+", at least 1.2 but below 1.5; and "+ +", at least 1.5.

As shown in Table 4, when the mixture solutions of IFN-α2 and IFN-α8 subtypes were allowed to act on HepG2 cells at the ratios of 4:6 and 2:8 (=IFN-α2:IFN-α8), the 2–5A synthetase induction activity exhibited substantially the same values as those estimated based on their additive action, while the induction activity exceeded the estimated values at the ratios of 8:2, 6:4 and 5:5 (=IFN-α2:IFN-α8), particularly, the activity showed higher activities at the ratios of 6:4 and 5:5 (=IFN-α2:IFN-α8). These results actually evidenced the finding from the measurement of anti-virus activity in Experiment 1-2.

EXAMPLE 1

Material Solution for Preparing Pharmaceuticals

Purified specimens of IFN-α2 and IFN-α8 subtypes, obtained by the methods in Experiments 1-1(a) and 1-1(b), were concentrated with a membrane filter in a usual manner, added to a physiological saline containing one percent (w/v) crystalline trehalose hydrate as a stabilizer into a solution that dissolved IFN-α2 and IFN-α8 subtypes in a ratio of 2:1 (=IFN-α2:IFN-α8) in a calculated total IFN-α activity of $1 \times 10^6$ IU/ml in terms of international unit. The resulting solution was sterilized with a membrane filter into a liquid preparation in a usual manner.

The product with a satisfactory stability is useful as a material solution used in preparing therapeutic, relieving and prophylactic agents, which are sensitive to protein synthesis inhibitory genes, for diseases such as those in immune systems, hematopoietic tissues, circulatory diseases, dermatological tissues, digestive organs, nervous systems, and muscles. Also the product can be used in research reagents and in preparing recombinant proteins as an inducer.

EXAMPLE 2
Material Solution for Preparing Pharmaceuticals

A solution of human IFN-α from BALL-1 cell, a human lymphoblastoid cell, commercialized by Cosmo Bio Co., Ltd., Tokyo, Japan, was fed to an anti-human IFN-α monoclonal antibody column chromatograph using "NK-2 SEPHAROSE", commercialized by Lonza, Switzerland, as a carrier, PBS (phosphate buffered saline) as a moving phase, and a 0.1M aqueous citric acid solution containing 0.3 M sodium chloride as an eluant, to remove calf serum albumin present in the human IFN-α solution and to obtain a purified human IFN-α specimen. Conventional analysis revealed that the purified specimen substantially consisted of IFN-α2 and IFN-α8 subtypes of IFN-α in an activity ratio of about 1:1 (=IFN-α2:IFN-α8) in terms of international units.

The above purified human IFN-α specimen was dialyzed against PBS, and the dialyzed inner solution was collected and concentrated in a usual manner. Then, the concentrated solution was mixed with a physiological saline containing one percent (w/v) of crystalline trehalose hydrate as a stabilizer to give an IFN-α activity of $5 \times 10^6$ IU/ml, and the resulting mixture was sterilized with a membrane filter into a liquid preparation.

The product with a satisfactory stability is useful as a material solution used for preparing therapeutic, relieving and prophylactic agents, which are sensitive to protein synthesis inhibitory genes, for diseases such as those in immune systems, hematopoietic tissues, circulatory diseases, dermatological tissues, digestive organs, nervous systems, and muscles. Also the product can be used in research reagents and in preparing recombinant proteins as an inducer.

EXAMPLE 3
Material Solution for Preparing Pharmaceuticals

Purified specimens of IFN-α2 and IFN-α8 subtypes, obtained according to the methods in Experiments 1-1(a) and 1-1(b), were in a usual manner concentrated with a membrane filter into solutions of either of the subtypes at a concentration of 2 mg/ml.

Pullulan having an average molecular weight of about 200,000, prepared according to the method as disclosed in Japanese Patent Kokai No. 65,302/94 applied for by the same applicant as the present invention, was in a usual manner decolored and desalted for purification, and lyophilized into a powder of purified pullulan. The powder was dissolved in PBS (pH 7.0) into a 20 mg/ml solution. The solution and a solution of one percent (w/v) cyanuric chloride in acetone were mixed in a ratio of 30:1 by volume, and the mixture was incubated while gently stirring for two hours under ice-chilled conditions to activate the pullulan by cyanuric chloride. The reaction mixture containing pullulan activated by cyanuric chloride and either of the above IFN-α2 and IFN-α8 solutions were mixed in a ratio of 1:1 (=IFN-α2:IFN-α8) by volume, and the resulting mixture was incubated at 37° C. for six hours under gentle stirring conditions to modify the subtype with pullulan. Thereafter, each reaction mixture was mixed with glycine to give a concentration of five percent (w/v) and incubated at 4° C. for 16 hours to suspend the reaction under gentle stirring conditions.

The reaction mixtures thus obtained were Respectively fractionated by feeding to a gel filration chromatograph, using "SEPHACRYL S-200 COLUMN", commercialized by Amersham Biosciences K.K., Tokyo, Japan, as a carrier for gel filtration, and PBS as a moving phase. The protein content in each fraction was analyzed by the Bradford method. As a result, two peaks with different retention times in each reaction mixture were observed. A fraction with a shorter retention time, which corresponded to a molecular weight of about 200,000 or higher, was collected and used as a fraction containing a pullulans-coupled subtype for either the IFN-α2 and IFN-α8 subtypes. The fractions containing pullulans-coupled subtypes were respectively subjected to chromatography using a polyclonal antibody column. The polyclonal antibody column was prepared in a usual manner by using a rabbit anit-human IFN-α polyclonal antibody, which had been prepared by using as an antigen a purified human IFN-α specimen obtained by the method in Example 2. By collecting fractions bound to the polyclonal antibody, purified specimens of pullulans-coupled subtype of either IFN-α2 end or IFN-α8 subtypes were respectively obtained. The purified specimens were respectively assayed for IFN-α activity in a conventional manner, and then mixed together in a ratio of 1:1 (=IFN-α:IFN-α8) in terms of international units and dialyzed against a physiological saline containing one percent (w/v) of crystalline trehalose hydrate as a stabilizer. The dialyzed inner solution was collected and adjusted to give $5 \times 10^4$ IU of IFN-α activity with a fresh preparation of the same physiological saline as above, and the resulting solution was sterilized with a membrane filter into a liquid preparation.

The product, which has satisfactory properties in stability in living bodies and relatively low antigenicity to the bodies, is useful as a material solution used in preparing therapeutic, relieving and prophylactic agents, which are sensitive to the expression of protein synthesis inhibitory genes, for diseases such as those in immune systems, hematopoietic tissues, circulatory diseases, dermatological tissues, digestive organs, nervous systems, and muscles. Also the product can be used in research reagents and in preparing recombinant proteins as an inducer.

EXAMPLE 4
Material Solution for Preparing Pharmaceuticals

Except for substituting a purified human IFN-α preparation prepared by the method in Example 2 for the IFN-α2 and IFN-α8 subtypes used in reacting pullulan activated by cyanuric chloride with either of the subtypes as shown in Example 3, the preparation was modified by reacting with pullulan according to Example 3, followed by purifying the reaction product on gel filtration chromatography and antibody column chromatography according to Example 3. Conventional analysis revealed that the resulting purified specimen of human IFN-α subtypes consisted essentially of pullulan-coupled IFN-α2 and IFN-α8 subtypes in an activity ratio of about 1:1 (=IFN-α2:IFN-α8) in terms of international unit. The purified specimen was dialyzed against physiological saline containing one percent (w/v) of crystalline trehalose hydrate as a stabilizer. The dialyzed inner solution was collected and adjusted to give $1 \times 10^5$ IU of IFN-α activity with a fresh preparation of the same physiological saline as above, and the resulting solution was sterilized with a membrane filter into a liquid preparation.

The product, which has satisfactory properties in stability in living bodies and relatively low antigenicity to the bodies, is useful as a material solution used in preparing therapeutic, relieving and prophylactic agents, which are sensitive to the expression of protein synthesis inhibitory genes, for diseases such as those in immune systems, hematopoietic tissues, circulatory diseases, dermatological tissues, digestive organs, nervous systems, and muscles. Also the product can be used in research reagents and in preparing recombinant proteins as an inducer.

EXAMPLE 5

Dried Injection

Material solutions for preparing pharmaceuticals, obtained in Examples 1 to 4, were respectively distributed to vials in a volume of one milliliter each, lyophilized and sealed. The products with satisfactory stability are useful as dried injections, which are sensitive to the expression of protein synthesis inhibitory genes, for treating, relieving and preventing diseases such as those in immune systems, hematopoietic tissues, circulatory diseases, dermatological tissues, digestive organs, nervous systems, and muscles.

EXAMPLE 6

Ointment

"HIBIS WOKO", a carboxy vinyl polymer commercialized by Wako Pure Chemical Industries, Tokyo, Japan, and crystalline trehalose hydrate were dissolved in sterilized distilled-water in respective concentrations of 1.4% (w/w) and 2.0% (w/w), and the resulting solution was mixed with "LUMIN" (alias NK-4, a photosensitizing dye commercialized by Hayashibara Biochemical Laboratories, Inc., Okayama, Japan) as a cell activator to give a concentration of 5 mg/g. The mixture was admixed with the material for pharmaceutical in Example 2 or 4 to give an IFN-α activity of $5 \times 10^4$ IU/g and then adjusted to pH 7.2 to obtain a gel composition.

The product, which has satisfactory extendibility, stability and cell activating activity, is useful as an ointment sensitive to the expression of protein synthesis inhibitory genes and is used for treating, relieving or preventing diseases such as those in immune systems, dermatological tissues, nervous systems, and muscles.

EXAMPLE 7

Tablet

"FINETOSE®", a crystalline maltose anhydride commercialized by Hayashibara Shoji Inc., Okayama, Japan, was mixed with the material solution for pharmaceutical in Example 2 or 4 to give an IFN-α activity of $1 \times 10^3$ IU/g, and the resulting mixture was in a usual manner tabletted into tablets, about 200 mg each.

The product, which is easily ingestible and satisfactorily stable, is useful as a tablet sensitive to the expression of protein synthesis inhibitory genes and is used for treating, relieving or preventing diseases such as those in immune systems, hematopoietic tissues, circulatory organs, dermatological tissues, digestive organs, nervous systems, and muscles.

INDUSTRIAL APPLICABILITY

As described above, the present invention was made based on the present inventors' self-finding that the coexistence of IFN-α2 and IFN-α8 subtypes of human IFN-α exerts synergism on the expression induction of protein synthesis inhibitory genes. Since the expression enhancer for protein synthesis inhibitory gene of the present invention comprises human IFN-α subtypes as effective ingredients which have been widely used in pharmaceuticals for humans, it can be advantageously used in pharmaceutical fields, particularly, those for diseases whose symptoms can be treated, relieved and prevented directly or indirectly through the gene expression of protein synthesis inhibitory genes. The expression enhancer can be also useful as a research reagent for analyzing molecular mechanism of expressing IFN activities and as an inducer for producing recombinant proteins.

The present invention with such outstanding effects and functions is a significant invention that greatly contributes to this art.

What is claimed is:

1. A method for enhancing the 2',5'-oligoadenylate synthetase gene expression and the double stranded RNA-dependent protein kinase gene expression, comprising a step of administering human IFN-α2 and IFN-α8 in an activity ratio of at least 1:0.25 but below 1:1.5 to a patient suffering from a condition selected from the group consisting of allergies, rheumatism, AIDS, leukemia, sarcoma, malignant melanoma, conjunctivitis, hepatitis, and enterocolitis.

* * * * *

SEQUENCE LISTING

```
<160> NUMBER OF SEQ ID NOS: 4

<210> SEQ ID NO 1
<211> LENGTH: 188
<212> TYPE: PRT
<213> ORGANISM: Homo sapiens
<220> FEATURE:
<221> NAME/KEY: Signal
<222> LOCATION: (1)...(23)
<220> FEATURE:
<221> NAME/KEY: Mature chain
<222> LOCATION: (24)...(188)
<300> PUBLICATION INFORMATION:
<308> DATABASE ACCESSION NUMBER: P01563 (Swissprot)

<400> SEQUENCE: 1

Met Ala Leu Thr Phe Ala Leu Leu Val Ala Leu Leu Val Leu Ser Cys
 1               5                  10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Lys Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80
```

```
Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Ser Leu Arg Ser Lys Glu
            180                 185

<210> SEQ ID NO 2
<211> LENGTH: 189
<212> TYPE: PRT
<213> ORGANISM: Homo sapiens
<220> FEATURE:
<221> NAME/KEY: Signal
<222> LOCATION: (1)...(23)
<220> FEATURE:
<221> NAME/KEY: Mature chain
<222> LOCATION: (24)...(189)
<300> PUBLICATION INFORMATION:
<308> DATABASE ACCESSION NUMBER: P32881 (Swissprot)

<400> SEQUENCE: 2

Met Ala Leu Thr Phe Tyr Leu Leu Val Ala Leu Val Val Leu Ser Tyr
  1               5                  10                  15

Lys Ser Phe Ser Ser Leu Gly Cys Asp Leu Pro Gln Thr His Ser Leu
                20                  25                  30

Gly Asn Arg Arg Ala Leu Ile Leu Leu Ala Gln Met Arg Arg Ile Ser
            35                  40                  45

Pro Phe Ser Cys Leu Lys Asp Arg His Asp Phe Glu Phe Pro Gln Glu
        50                  55                  60

Glu Phe Asp Asp Lys Gln Phe Gln Lys Ala Gln Ala Ile Ser Val Leu
65                  70                  75                  80

His Glu Met Ile Gln Gln Thr Phe Asn Leu Phe Ser Thr Lys Asp Ser
                85                  90                  95

Ser Ala Ala Leu Asp Glu Thr Leu Leu Asp Glu Phe Tyr Ile Glu Leu
            100                 105                 110

Asp Gln Gln Leu Asn Asp Leu Glu Ser Cys Val Met Gln Glu Val Gly
        115                 120                 125

Val Ile Glu Ser Pro Leu Met Tyr Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Ser Cys Ala Trp Glu Val Val Arg Ala Glu Ile Met Arg Ser Phe Ser
                165                 170                 175

Leu Ser Ile Asn Leu Gln Lys Arg Leu Lys Ser Lys Glu
            180                 185

<210> SEQ ID NO 3
<211> LENGTH: 1733
<212> TYPE: DNA
<213> ORGANISM: Homo sapiens
```

```
<220> FEATURE:
<221> NAME/KEY: CDS
<222> LOCATION: (511)...(1077)
<220> FEATURE:
<221> NAME/KEY: sig_peptide
<222> LOCATION: (511)...(579)
<220> FEATURE:
<221> NAME/KEY: mat_peptide
<222> LOCATION: (580)...(1074)
<300> PUBLICATION INFORMATION:
<308> DATABASE ACCESSION NUMBER: J00207 (GenBank)

<400> SEQUENCE: 3
```

| | | | | | |
|---|---|---|---|---|---|
| gcgcctctta | tgtacccaca | aaaatctatt | ttcaaaaaag | ttgctctaag | aatatagtta | 60 |
| tcaagttaag | taaaatgtca | atagcctttt | aatttaattt | ttaattgttt | tatcattctt | 120 |
| tgcaataata | aaacattaac | tttatacttt | ttaatttaat | gtatagaata | gagatataca | 180 |
| taggatatgt | aaatagatac | acagtgtata | tgtgattaaa | atataatggg | agattcaatc | 240 |
| agaaaaagt | ttctaaaaag | gctctggggt | aaaagaggaa | ggaaacaata | atgaaaaaaa | 300 |
| tgtggtgaga | aaaacagctg | aaaacccatg | taaagagtgt | ataaagaaag | caaaaagaga | 360 |
| agtagaaagt | aacacagggg | catttggaaa | atgtaaacga | gtatgttccc | tatttaaggc | 420 |
| taggcacaaa | gcaaggtctt | cagagaacct | ggagcctaag | gtttaggctc | acccatttca | 480 |
| accagtctag | cagcatctgc | aacatctaca | atggccttga | cctttgcttt | actggtggcc | 540 |
| ctcctggtgc | tcagctgcaa | gtcaagctgc | tctgtgggct | gtgatctgcc | tcaaacccac | 600 |
| agcctgggta | gcaggaggac | cttgatgctc | ctggcacaga | tgaggagaat | ctctcttttc | 660 |
| tcctgcttga | aggacagaca | tgactttgga | tttccccagg | aggagtttgg | caaccagttc | 720 |
| caaaaggctg | aaaccatccc | tgtcctccat | gagatgatcc | agcagatctt | caatctcttc | 780 |
| agcacaaagg | actcatctgc | tgcttgggat | gagaccctcc | tagacaaatt | ctacactgaa | 840 |
| ctctaccagc | agctgaatga | cctggaagcc | tgtgtgatac | agggggtggg | ggtgacagag | 900 |
| actccctga | tgaaggagga | ctccattctg | gctgtgagga | aatacttcca | aagaatcact | 960 |
| ctctatctga | aagagaagaa | atacagccct | tgtgcctggg | aggttgtcag | agcagaaatc | 1020 |
| atgagatctt | tttctttgtc | aacaaacttg | caagaaagtt | taagaagtaa | ggaatgaaaa | 1080 |
| ctggttcaac | atggaaatga | ttttcattga | ttcgtatgcc | agctcacctt | tttatgatct | 1140 |
| gccatttcaa | agactcatgt | ttctgctatg | accatgacac | gatttaaatc | ttttcaaatg | 1200 |
| tttttaggag | tattaatcaa | cattgtattc | agctcttaag | gcactagtcc | cttacagagg | 1260 |
| accatgctga | ctgatccatt | atctatttaa | atattttaa | aatattattt | atttaactat | 1320 |
| ttataaaaca | acttattttt | gttcatatta | tgtcatgtgc | acctttgcac | agtggttaat | 1380 |
| gtaataaaat | gtgttctttg | tatttggtaa | atttattttg | tgttgttcat | tgaacttttg | 1440 |
| ctatggaact | tttgtacttg | tttattcttt | aaaatgaaat | tccaagccta | attgtgcaac | 1500 |
| ctgattacag | aataactggt | acacttcatt | tgtccatcaa | tattatattc | aagatataag | 1560 |
| taaaaataaa | ctttctgtaa | accaagttgt | atgttgtact | caagataaca | gggtgaacct | 1620 |
| aacaaataca | attctgctct | cttgtgtatt | tgattttgt | atgaaaaaaa | ctaaaaatgg | 1680 |
| taatcatact | taattatcag | ttatggtaaa | tggtatgaag | agaagaagga | acg | 1733 |

```
<210> SEQ ID NO 4
<211> LENGTH: 633
<212> TYPE: DNA
<213> ORGANISM: Homo sapiens
<220> FEATURE:
<221> NAME/KEY: CDS
```

-continued

```
<222> LOCATION: (48)...(617)
<220> FEATURE:
<221> NAME/KEY: sig_peptide
<222> LOCATION: (48)...(116)
<220> FEATURE:
<221> NAME/KEY: mat_peptide
<222> LOCATION: (117)...(614)
<300> PUBLICATION INFORMATION:
<308> DATABASE ACCESSION NUMBER: X03125 (GenBank)

<400> SEQUENCE: 4 agggtcatc  catctgaacc  agctcagcag  catccacaac  atctacaatg  gccttgactt      60
tttatttact  ggtggccta   gtggtgctca  gctacaagtc  attcagctct  ctgggctgtg    120
atctgcctca  gactcacagc  ctgggtaaca  ggagggcctt  gatactcctg  gcacaaatgc    180
gaagaatctc  tcctttctcc  tgcctgaagg  acagacatga  ctttgaattc  ccccaggagg    240
agtttgatga  taaacagttc  cagaaggctc  aagccatctc  tgtcctccat  gagatgatcc    300
agcagacctt  caacctcttc  agcacaaagg  actcatctgc  tgctttggat  gagacccttc    360
tagatgaatt  ctacatcgaa  cttgaccagc  agctgaatga  cctggagtcc  tgtgtgatgc    420
aggaagtggg  ggtgatagag  tctcccctga  tgtacgagga  ctccatcctg  gctgtgagga    480
aatacttcca  aagaatcact  ctatatctga  cagagaagaa  atacagctct  tgtgcctggg    540
aggttgtcag  agcagaaatc  atgagatcct  tctctttatc  aatcaacttg  caaaaaagat    600
tgaagagtaa  ggaatgagac  ctggtacaac  acg                                   633
```